United States Patent
Cannon et al.

(10) Patent No.: US 11,331,208 B2
(45) Date of Patent: May 17, 2022

(54) INNER CATHETER WITH A PUSHER BAND

(71) Applicant: Cook Medical Technologies LLC, Bloomington, IN (US)

(72) Inventors: Tiffani Cannon, Bloomington, IN (US); Brent A Mayle, Spencer, IN (US); James C Merk, Terre Haute, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 262 days.

(21) Appl. No.: 14/196,664

(22) Filed: Mar. 4, 2014

(65) Prior Publication Data
US 2014/0257456 A1 Sep. 11, 2014

Related U.S. Application Data (60) Provisional application No. 61/772,807, filed on Mar. 5, 2013.

(51) Int. Cl.
*A61F 2/966* (2013.01)

(52) U.S. Cl.
CPC ...... *A61F 2/966* (2013.01); *A61F 2002/9665* (2013.01); *A61F 2220/005* (2013.01); *A61F 2220/0058* (2013.01)

(58) Field of Classification Search
CPC .......... A61F 2/962; A61F 2/966; A61F 2/954; A61F 2/852; A61F 2/95; A61F 2002/9665; A61F 2002/9505; A61F 2002/9522; A61F 2002/9534; A61F 2220/0058; A61F 2/243; A61F 2/2436; A61F 2/2439; A61F 2002/9511; A61F 2002/9517; A61F 2002/9528; A61F 2/958; A61F 2/97; A61F 2002/9538; A61F 2002/9586
USPC ......................................................... 623/1.12
See application file for complete search history.

(56) References Cited

U.S. PATENT DOCUMENTS

| | | | |
|---|---|---|---|
| 5,104,399 A | | 4/1992 | Lazarus |
| 5,733,325 A | * | 3/1998 | Robinson ............... A61F 2/07 623/1.11 |
| 5,782,909 A | | 7/1998 | Quiachon et al. |
| 5,833,694 A | | 11/1998 | Poncet |
| 5,989,280 A | | 11/1999 | Euteneuaer et al. |
| 6,183,481 B1 | * | 2/2001 | Lee ........................ A61F 2/954 606/108 |

(Continued)

FOREIGN PATENT DOCUMENTS

DE 3217006 11/1983

*Primary Examiner* — Katherine H Schwiker
(74) *Attorney, Agent, or Firm* — Crowell & Moring LLP (57) ABSTRACT

An inner catheter for deployment of a medical device can include a pusher band having a passage that includes a first portion extending from a first end to a position and a second portion extending from a second end to the position. A cross-sectional area of the second portion can be less than a cross-sectional area of the first portion to form a step. A second end of the first tubular member having first and second ends can be within the first portion of the pusher band, abut the step and be unable to pass through the second portion. A portion of a second tubular member having first and second ends can be within the pusher band, and the second end of the second tubular member can extend away from the second end of the pusher band and be configured to extend through a medical device.

3 Claims, 5 Drawing Sheets

(56) References Cited

U.S. PATENT DOCUMENTS

| | | | |
|---|---|---|---|
| 6,416,536 B1 | 7/2002 | Yee | |
| 6,652,569 B1 | 11/2003 | Taylor et al. | |
| 6,669,719 B2 * | 12/2003 | Wallace | A61B 17/1214 606/108 |
| 6,827,730 B1 * | 12/2004 | Leschinsky | A61F 2/95 606/108 |
| 7,435,253 B1 * | 10/2008 | Hartley | A61F 2/07 623/1.11 |
| 7,527,643 B2 | 5/2009 | Case et al. | |
| 7,942,924 B1 * | 5/2011 | Perez | A61F 2/95 623/1.23 |
| 2001/0049547 A1 | 12/2001 | Moore | |
| 2004/0133264 A1 * | 7/2004 | Moore | A61F 2/966 623/1.12 |
| 2006/0100687 A1 * | 5/2006 | Fahey | A61F 2/95 623/1.11 |
| 2006/0142704 A1 * | 6/2006 | Lentz | 604/264 |
| 2007/0282421 A1 | 12/2007 | Parker et al. | |
| 2008/0161902 A1 | 7/2008 | Poulsen | |
| 2009/0030497 A1 * | 1/2009 | Metcalf | A61F 2/95 623/1.12 |
| 2009/0204197 A1 | 8/2009 | Dorn et al. | |
| 2012/0078350 A1 * | 3/2012 | Wang | A61F 2/2436 623/2.11 |
| 2012/0296409 A1 * | 11/2012 | Kawakita | A61F 2/915 623/1.12 |
| 2012/0310320 A1 * | 12/2012 | Gill et al. | 623/1.11 |
| 2013/0073024 A1 * | 3/2013 | Russo | A61F 2/966 623/1.11 |
| 2013/0226276 A1 * | 8/2013 | Newell | A61F 2/82 623/1.11 |

* cited by examiner

INNER CATHETER WITH A PUSHER BAND

This application claims priority to U.S. Provisional Application No. 61/772,807, filed Mar. 5, 2013, which is hereby incorporated by reference herein.

BACKGROUND

The present invention relates generally to medical devices and more particularly to delivery systems that include inner catheters that have a pusher band for introducing a medical device into a patient.

Delivery systems are widely used for delivering an implantable medical device such as a stent to a deployment site within the vasculature of a patient. Deployment of stents and other medical interventional devices is now a routine practice, and such deployment is often carried out with only a minimum of complications, if any. This is particularly true when such devices have a relatively short length (e.g., less than about 80 mm) and/or a relatively modest outer diameter. However, as medical technology has progressed, stents and other interventional devices having longer lengths (e.g., about 100 to 300 mm or more) and/or having outer coatings, coverings, etc., that increase the effective outer surface of the stent have become more common. When such stents are placed in a sheath lumen for delivery to the target site, the greater length and/or outer surface of the stent increases the frictional forces between the sheath and the stent thereby increasing deployment forces necessary to extract the stent from the sheath when compared to stents that are shorter and/or have lesser outer surface. In addition, if an introducer with a smaller inner diameter is used, an increased force to further compress the stent or medical device can further translate to increased resistance to deployment.

Delivery systems often include an outer sheath with an inner catheter inside of the outer sheath. The stent is positioned within the outer sheath such that the inner catheter extends though the stent. The inner catheter also has a pusher band adjacent to a proximal end of the stent. To deploy the stent, the outer sheath can be retracted relative to the inner catheter thereby deploying the stent. During deployment, the stent exerts a force on the pusher band. As described above, longer length stents can require more force to be able to be deployed. Thus, the increased force used may cause components of the inner catheter to deform which can cause the stent to not deploy at the intended treatment site. For example, the deformation of the inner catheter can cause the stent to move during deployment. The increased force can cause compression of the inner catheter and the pusher band and lead to a "spring" force, which can lead to a non-uniform deployment as the spring force is released and cause inaccurate deployment and possible fracturing of the stent. When substantial deformation occurs, deployment of the stent can even be prevented. Therefore, the inventors believe an improved inner catheter to deploy medical devices would be desirable.

SUMMARY

An inner catheter for deployment of a medical device is provided. The inner catheter can include a pusher band having a passage extending from a first end to a second end of the pusher band. The passage can include a first portion extending from the first end to a position between the first end and the second end, and a second portion extending from the second end to the position. The first portion can have a first cross-sectional area and the second portion can have a second cross-sectional area less than the first cross-sectional area to form a step at the position. The inner catheter can also include a first elongated tubular member coupled to the pusher band and comprising a first end and a second end. The second end of the first tubular member can be within the first portion of the passage of the pusher band and abut the step such that the second end of the first tubular member is unable to pass through the second portion. The inner catheter can further include a second elongated tubular member comprising a first end and a second end. A portion of the second tubular member can be within the passage of the pusher band and the second end of the second tubular member can extend away from the second end of the pusher band and can be configured to extend through a medical device.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
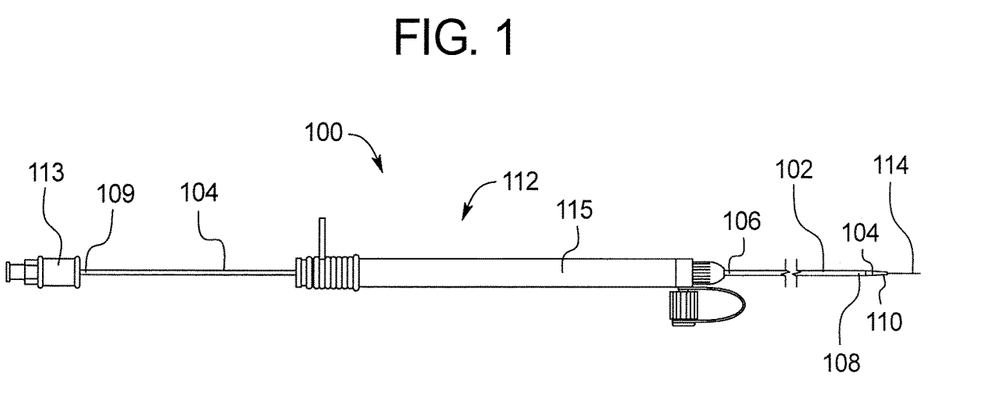
FIG. 1 is a side view of delivery system that includes an outer sheath and an inner catheter.

Referring now to the figures, and particularly to FIG. 1, a delivery system 100 that includes an outer sheath 102 and an inner catheter 104 is shown. The outer sheath 102 has a passage extending from a first end 106 to a second end 108, and the inner catheter 104 is within the passage of the outer sheath 102. The inner catheter 104 can also have a passage extending from a first end 109 to a second end 110. The first end 106 of the outer sheath 102 and the first end 109 of the inner catheter 104 can be coupled to a handle 112. For instance, the first end 109 of the inner catheter 104 can be coupled to a first handle member 113, and the first end 106 of the outer sheath 102 can be coupled to a second handle member 115. The first handle member 113 and the second handle member 115 can be moved longitudinally relative to one another so that the inner catheter 104 and the outer sheath 102 can move longitudinally relative to one another. A guide wire 114 can be used to reach a target site within a patient that the medical device is to be deployed. The delivery system 100 can be slid over the guide wire 114 such that the guide wire 114 extends though the passage of the inner catheter 104.

Figure 2:
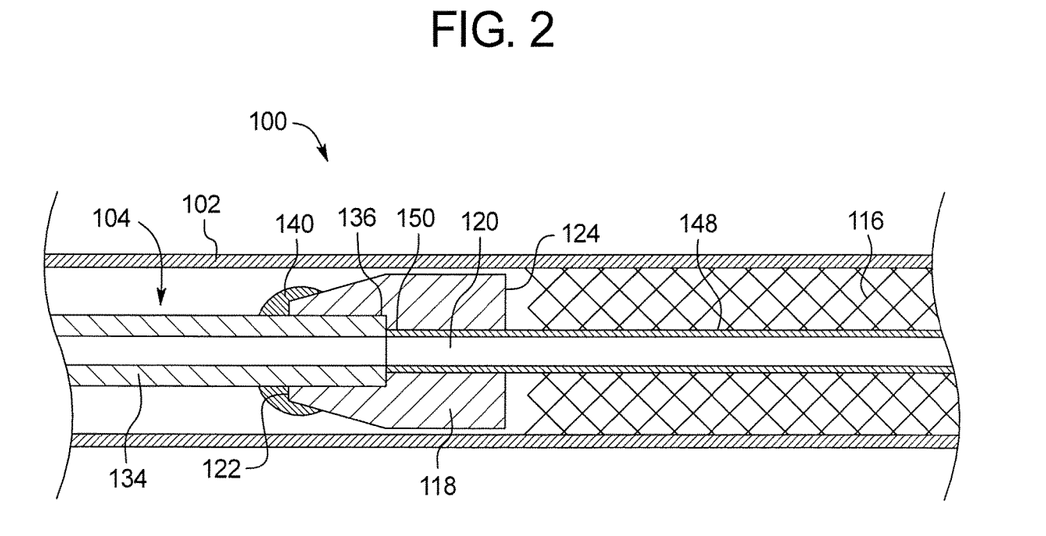
FIG. 2 is a cross-sectional side view of a portion of a delivery system showing an inner catheter with a pusher band.
Figure 3:
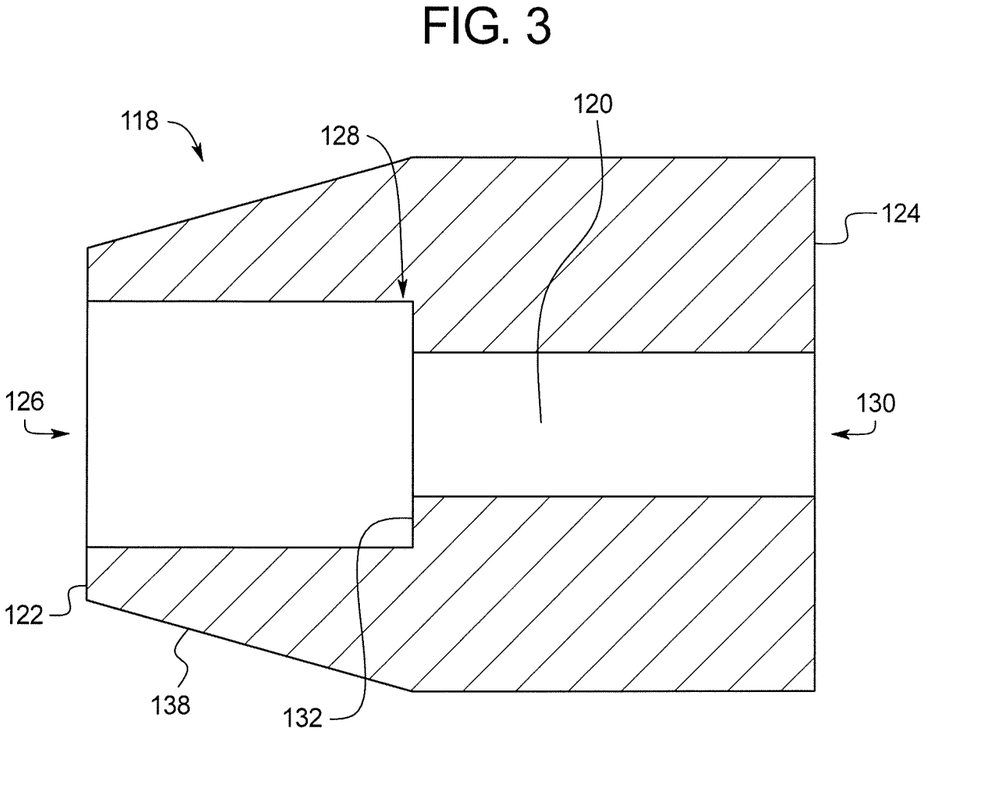
FIG. 3 is a blown up cross-sectional side view of the pusher band of FIG. 2 showing a step in the passageway of the pusher band.

FIG. 2 is a cross-sectional view of a section of the delivery system 100 near the second end 110 of the inner catheter 104 and the second end 108 of the outer sheath 102 with a medical device 116 positioned inside of the outer sheath 102. The inner catheter 104 includes a pusher band 118 having a passage 120 extending from a first end 122 to a second end 124 of the pusher band 118. FIG. 3 is a blown up cross-sectional view of the pusher band 118 to further show the structure of the pusher band 118. The passage 120 has a first portion 126 extending from the first end 122 to a position 128 between the first end 122 and the second end 124. The passage 120 can also have a second portion 130 extending from the second end 124 to the position 128. The first portion 126 can have a first cross-sectional area, and the second portion 130 can have a second cross-sectional area less than the first cross-sectional area to form a step 132 at the position 128. Furthermore, the first end 122 of the pusher band 118 can be a proximal end, and the second end 124 of the pusher band 118 can be a distal end.

As shown in FIG. 2, the passage 120 of the pusher band 118 can be configured to engage with a first elongated tubular member 134. The first tubular member 134 can be coupled to the pusher band 118 and have a first end (not shown) and a second end 136. The second end 136 can be within the first portion 126 of the pusher band 118 and can abut the step 132 such that the second end 136 of the first tubular member 134 is unable to pass through the second portion 130 of the pusher band 118. For example, the first portion 126 can have a first diameter, and the second portion 130 can have a second diameter less than the first diameter. The first end 136 of the first tubular member 134 can snugly fit within the first portion 126 such that the first end has an outer diameter similar to the first diameter of the first portion 126 of the pusher band 118.

During deployment of the medical device 116, the first tubular member 134 can experience a compressive force as a result of the pusher band 118 pushing against the medical device 116. As such, the step 132 of the pusher band 118 can provide a structure to prevent the second end 136 of the first tubular member 134 from sliding though the second portion 130 of the passage 120 of the pusher band 118. Therefore, various configurations of the step 132 are possible. For example, the size of the step can vary depending on the size of the first tubular member 134 and a second tubular member 148 (described below). In further examples, the step 132 can form an annulus, or the step 132 can be discontinuous. Generally, the step 132 provides sufficient structure for the first tubular member 134 to abut against. Therefore, since the step 132 provides structural support, the first tubular member 134 may not need to be as securely attached to the pusher band 118 than if the pusher band 118 did not include the step 132.

A further advantage of the step 132 is that the second end 136 of the first tubular member 134 is covered by the pusher band 118. For instance, the second end 136 of the first tubular member 134 may have sharp edges that are covered by the pusher band 118. For example, a cut metal tube may be used as the first tubular member 134 which may have sharp edges. Another advantage is that dissimilar materials can be more easily joined together. For example, the first tubular member 134 may be a different material than the material of the second tubular member 148.

To further improve rigidity of the inner catheter 104, the pusher band 118 and/or the first tubular member 134 can comprise a metal or be formed of a metal or metal alloy. For example, the metal or metal alloy can be steel, titanium or nitinol, and the pusher band 118 can be made by various manufacturing methods such as machining or casting. The pusher band 118 and the first tubular member 134 can be coupled to one another by attachment methods such as adhesive or fasteners. When the first tubular member 134 and the pusher band 118 comprise a metal, the first tubular member 134 and the pusher band 118 can be bonded to one another. For example, the pusher band 118 can be bonded or be metallurgically coupled to the first tubular member 134 by welding, soldering or brazing. The first tubular member 134 and the pusher band 118 may be entirely a metal or metal alloy or only a portion may be a metal or metal alloy. For example, a portion of the first tubular member 134 and/or the pusher band 118 may have a first section that is a metal or metal alloy to provide improved stiffness while a second section may have a lower stiffness than the metal or metal alloy. For example, the second section may be formed of a polymeric material.

An outer surface 138 of the pusher band 118 that forms the first portion 126 of the pusher band 118 can be tapered. For example, a wall thickness of the first portion 126 of the pusher band 118 at the first end 122 can be less than a wall thickness of the first portion 126 away from the first end 122. The tapered can provide additional space between the pusher band 118 and the outer sheath 102 so that the pusher band 118 can be bonded to the first tubular member 134 without a bonding material extending to the outer sheath 102. For example, FIG. 2 illustrates solder 140 that can be used to bond the first end 122 of the pusher band 118 to the first tubular member 134. The taper of the first end 122 of the pusher band 118 provides space for the solder 140 to reside without contacting the outer sheath 102. In another example, a jacket such as a polymer jacket can bond the first end 122 of the pusher band 118 to the first tubular member 134. Adhesives, glues and melted polymers are additional examples of how the first end 122 of the pusher band 118 can be bonded to the first tubular member 134.

Figure 4:
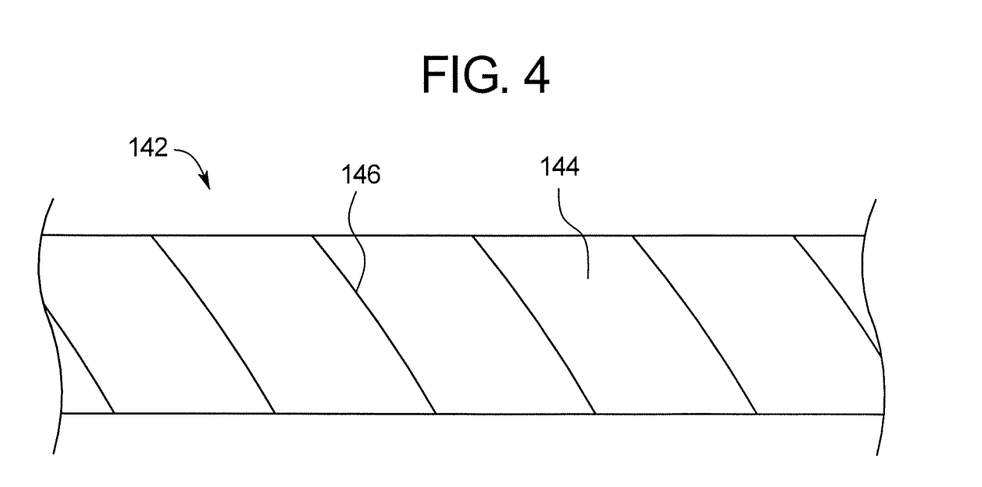
FIG. 4 is a side view of a section of an example cable tube that can be used as a first tubular member of an inner catheter.

FIG. 4 is a side view of a section of an example of a cable tube 142 that can be used as the first tubular member 134. The cable tube 142 can comprise a helical coil having windings 144 in which neighboring winding 144 contact one another when the cable tube 142 is in a relaxed state. The interface 146 between neighboring windings 144 can open when the cable tube 142 is bent thereby providing flexibility to the cable tube 142. Thus, the inner catheter 104 can bend and flex as the delivery system 100 is navigated though a vessel within a patient. Then, when the medical device 116 is deployed and a compressive force is applied to the cable tube 142, a compressive force between the windings 144 is created and the cable tube 142 may not substantially longitudinally deform. For example, the cable tube 142 can be formed of a metal or metal alloy and provide longitudinal stiffness for deployment while providing radial flexibility for navigation through a vessel.

Referring back to FIG. 2, the inner catheter 104 can also include a second elongated tubular member 148 comprising a first end 150 and a second end 110. A portion of the second tubular member 148 can be within the passage 120 of the pusher band 118, and the second end 110 of the second tubular member 148 can extend away from the second end 124 of the pusher band 118. The pusher band 118 can provide structural support between the first tubular member 134 and the second tubular member 148. The second tubular member 148 can be configured to extend through the medical device 116. Furthermore, the second end 110 of the second tubular member 148 can extend out of the second end 108 of the outer sheath 102 and have an atraumatic tip. The second tubular member 148 can also provide a passage for the guide wire 114 to extend out of the distal end of the delivery system. During deployment of the medical device 116, the second tubular member 148 may not experience forces as large as the forces that the first tubular member 134 experiences. Therefore, the second tubular member 148 may not necessarily be coupled to the pusher band 118 as securely as the first tubular member 134. For example, the second tubular member 148 may be attached to the pusher band 118 with an adhesive. As such, the second tubular member 148 may be formed of a material that has a lower stiffness than the stiffness of the material that the first tubular member 134 is formed of. For example, the second tubular member 148 can be formed from a polymeric material such as polyether ether ketone (PEEK), polyamide (e.g., nylon) or poly-fluorocarbon (e.g., tetrafluoroethylene, fluorinated ethylene propylene, or perfluoroalkoxy).

As illustrated in FIG. 2, the first end 150 of the second tubular member 148 can abut the second end 136 of the first tubular member 134. The first tubular member 134 and the second tubular member 148 can form a passage that is smooth without transitions so that the guide wire 114 can be easily slide though the inner catheter 104. For example, a wall thickness of the second end 136 of the first tubular member 134 can be about equal to the sum of a wall thickness of the first end 150 of the second tubular member 148 and a depth of the step 132. However, the first end 150 of the second tubular member 148 may be alternatively positioned anywhere within the passage 120 of the pusher band 118 or can even be positioned within first tubular member 134.

Figure 5:
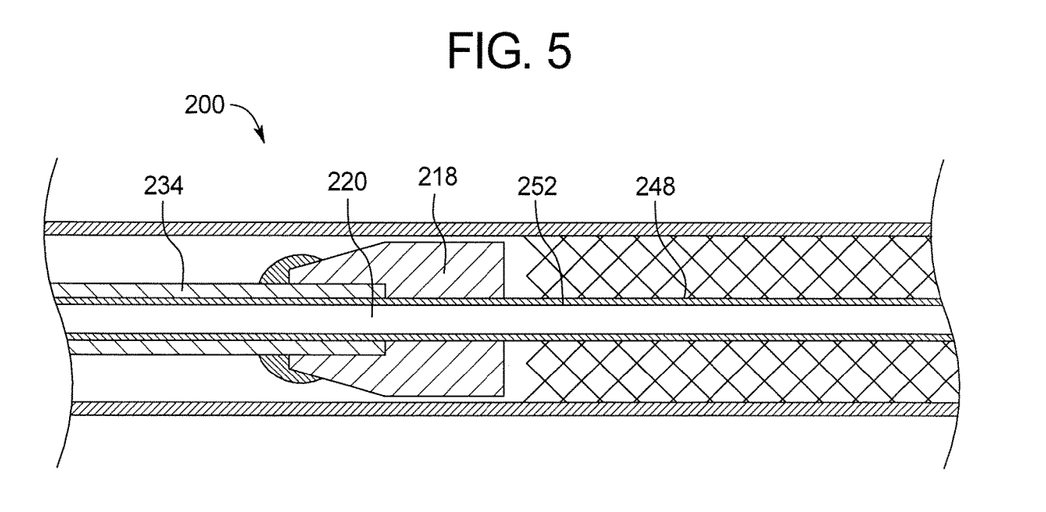
FIG. 5 is a cross-sectional side view of another example of a delivery system that includes an inner catheter having a first tubular member with a second tubular member that extends into the first tubular member.

FIG. 5 illustrates another configuration of a delivery system 200 similar to the delivery system 100 of FIG. 2. The delivery system 200 includes a pusher band 218, a first tubular member 234 and a second tubular member 248. The second tubular member 248 extends into the first tubular member 234. Furthermore, the second tubular member 248 can be decoupled from or not attached to the pusher band 218. The second tubular member 248 can, in effect, float within the passage 220 of the pusher band 218. Furthermore, the second tubular member 248 can extend though the first tubular member 234. The first end of the second tubular member 248 can be coupled to a handle. The first end of the first tubular member 234 can also be coupled to the handle. For example, the first tubular member 234 and the second tubular member 248 can be coupled to a first handle member. Since the second tubular member 248 can extend entirely through the first tubular member 234, the second tubular member 248 can provide a passageway that is smooth for a guide wire to pass through. Furthermore, an interior surface 252 of the second tubular member 248 can have a relatively low coefficient of friction. For example, the second tubular member 248 may be formed of a low friction material or have a coating within the second tubular member 248. For instance, the second tubular member 248 may be formed or have a coating of a polymeric material such as polyether ether ketone (PEEK), polyamide (e.g., nylon) or poly-fluorocarbon (e.g., tetrafluoroethylene, fluorinated ethylene propylene, or perfluoroalkoxy) or other lubricious polymers or blends thereof.

Figure 6:
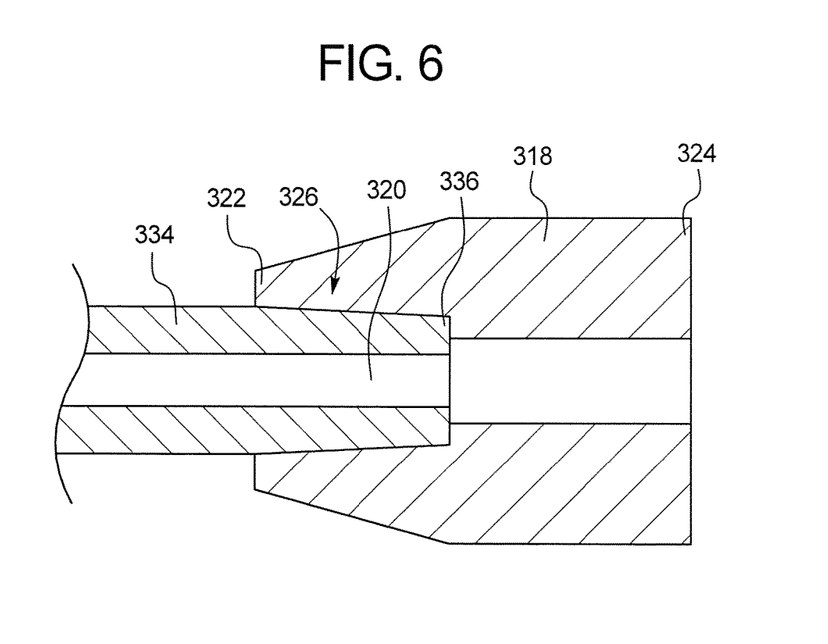
FIG. 6 is a cross-sectional side view of an example of a first tubular member having an outer surface angled toward the passage and a pusher band having a first portion of the passage having a corresponding angle.

The inner surfaces of the passage 120 of the pusher band 118 can be substantially parallel to one another, as illustrated in FIGS. 2, 3 and 5. However, the inner surfaces may be non-parallel to one another. For example, the inner surfaces of the first portion 126 and/or the second portion 130 of the pusher band 118 can be tapered or have a conical shape. For instance, the inner surface of the first portion 126 from the first end 122 toward the second end 124 can be angled inward or outward from the passage 120. FIG. 6 is one example in which the inner surface of the first portion 326 of the pusher band 318 can be, from the first end 322 toward the second end 324, angled towards the passage 320. The second end 336 of the first tubular member 334 may have a corresponding outer surface that, from the first end to the second end 336, angles toward the passage 320. Therefore, the second end 336 of the first tubular member 224 can be more easily inserted into the first portion 326 of the pusher band 318 since the second end 336 of the first tubular member 334 can have a smaller diameter than a diameter of the passage 320 at the first end 322.

Figure 7:
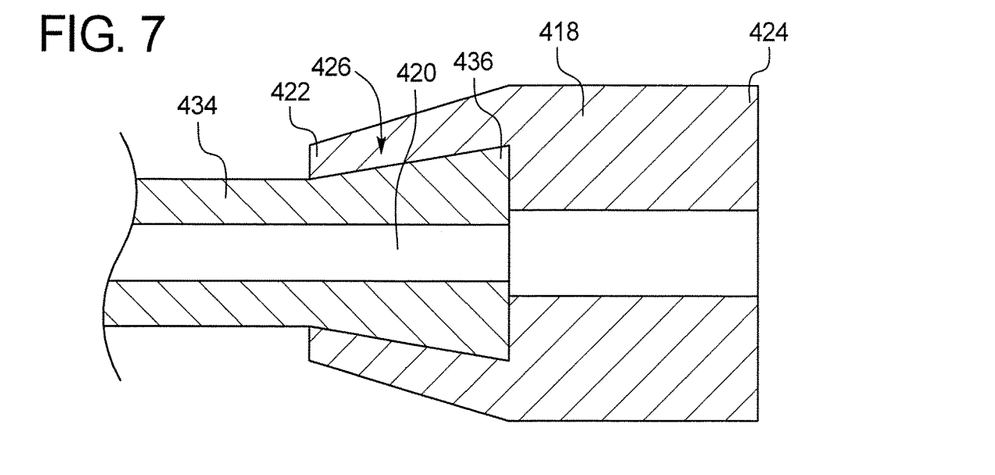
FIG. 7 is a cross-sectional side view of an example of a first tubular member having an outer surface angled away from the passage and a pusher band having a first portion of the passage having a corresponding angle.

FIG. 7 is example in which the inner surface of the first portion 426 of the pusher band 418 can be, from the first end 422 toward the second end 424, angled away from the passage 420. The second end 436 of the first tubular member 434 may have a corresponding outer surface that, from the first end to the second end 436, angles away from the passage 420. Therefore, after the second end 436 is inserted into the first portion 426 of the pusher band 418, the first tubular member 434 and the pusher band 418 may resist separation since the second end 436 of the first tubular member 434 can have a larger diameter than a diameter of the passage 420 at the first end 422. The second end 436 of the first tubular member 434 can be coupled to the first portion 426 of the pusher band 418 by various methods. For example, the second end 436 of the first tubular member 434 can be elastically compressed and inserted into the first portion 426 of the pusher band 418. Alternatively, the first portion 426 of the pusher band 418 can be formed around the second end 436 of the first tubular member 434. The inner surface of the first portion 326, 426 of the passage 320, 420 and the outer surface of the second end 336, 436 of first tubular member 334, 434 can also have other configurations that correspond to one another other than those illustrated in FIGS. 6 and 7.

Figure 8:
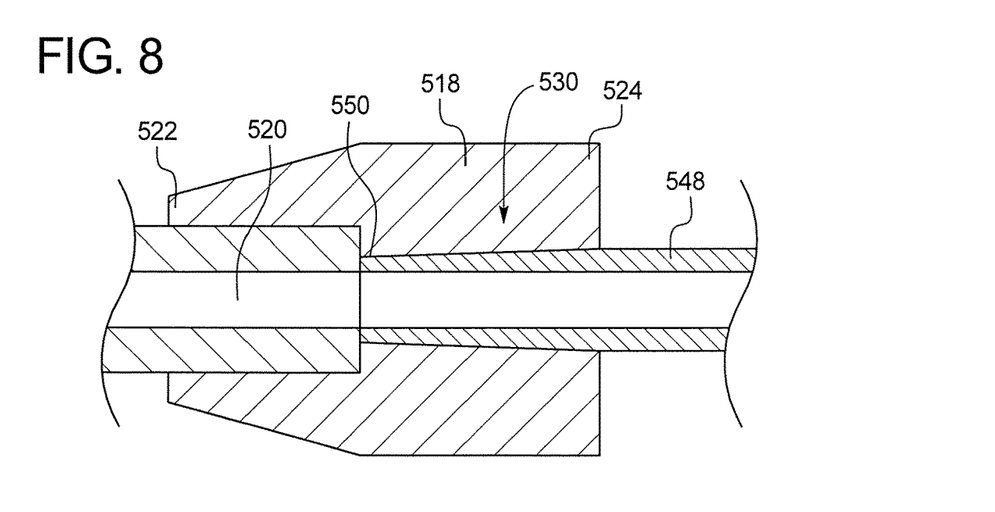
FIG. 8 is a cross-sectional side view of an example of a second tubular member having an outer surface angled toward the passage and a pusher band having a second portion of the passage having a corresponding angle.
Figure 9:
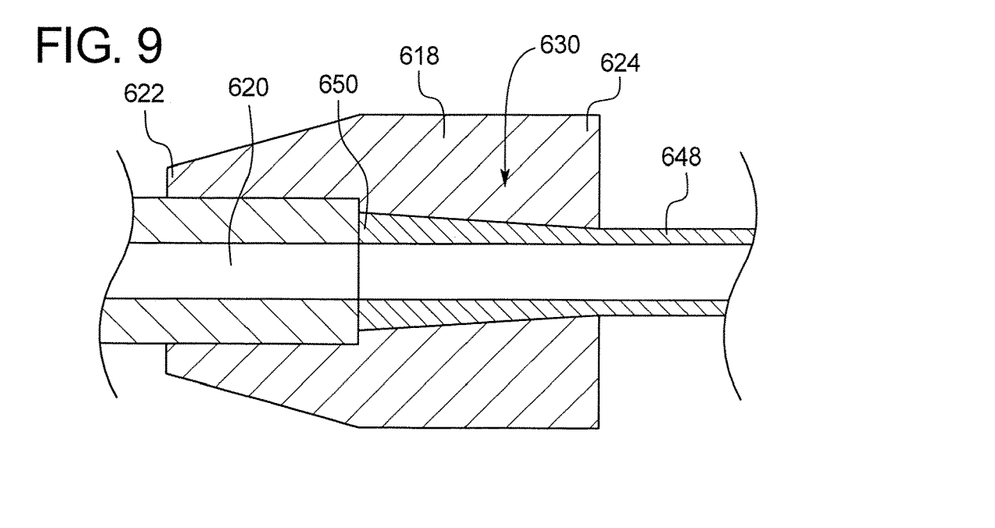
FIG. 9 is a cross-sectional side view of an example of a second tubular member having an outer surface angled away from the passage and a pusher band having a second portion of the passage having a corresponding angle.
Figure 10A:
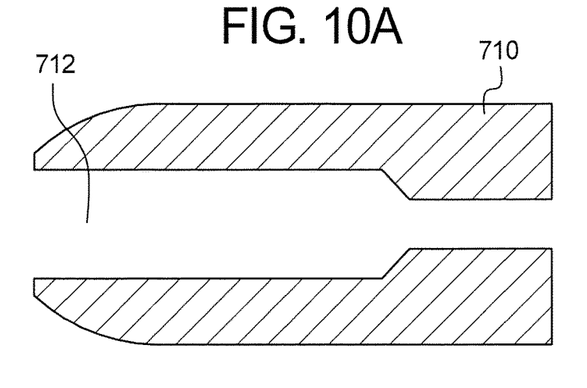
FIGS. 10A-E are cross-sectional side views of examples of pusher bands showing different configurations.
Figure 10B:
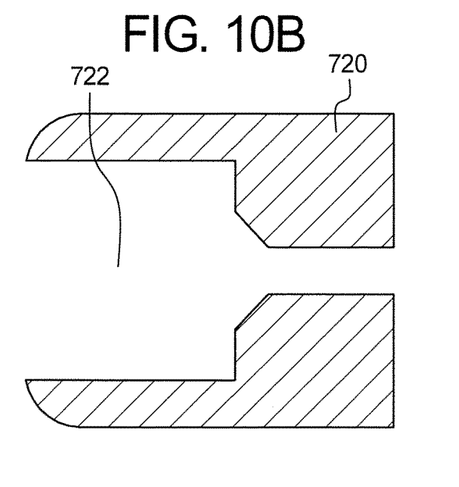
Figure 10C:
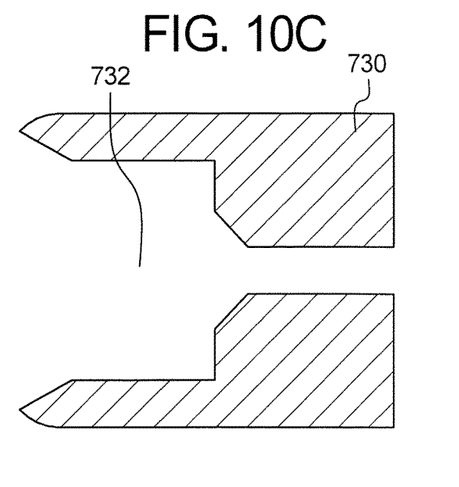
Figure 10D:
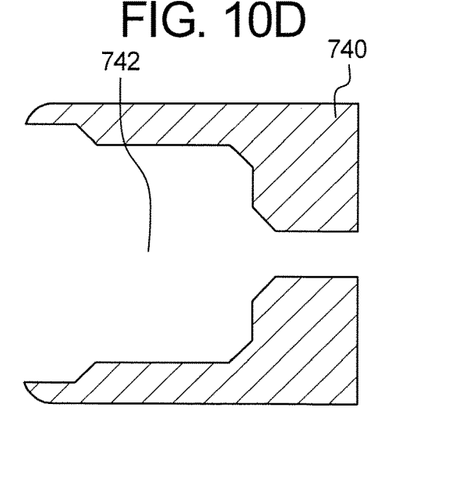
Figure 10E:
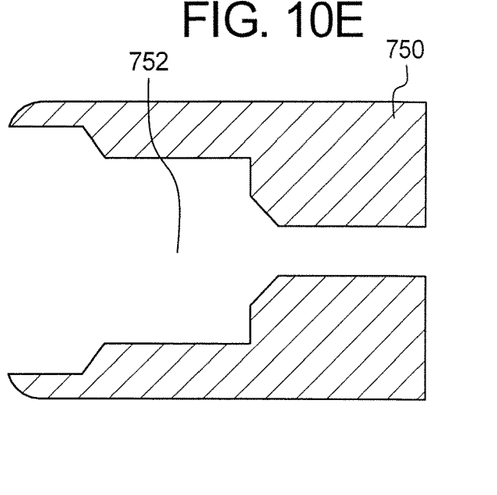

When the first end 150 of the second tubular member 148 is within the passage 120 of the pusher band 118, the inner surface of the second portion 130 of the pusher band 118 can be tapered in addition to or alternatively to the first portion 126 being tapered. FIG. 8 is an example in which the inner surface of the second portion 530 of the pusher band 518 can be, from the second end 524 toward the first end 522, angled towards the passage 520. The first end 550 of the second tubular member 548 may have a corresponding outer surface that, from the second end to the first end 550, angles toward the passage 520. One advantage of the angled second portion 530 of FIG. 8 is that the angled surface can prevent the first end 550 of the second tubular member 548 from being able to pass through the passage 520 to the first end 522 of the pusher band 528. FIG. 9 is an example in which the inner surface of the second portion 630 of the pusher band 618 can be, from the second end 624 toward the first end 622, angled away from the passage 620. The first end 650 of the second tubular member 648 may have a corresponding outer surface that, from the second end to the first end 650, angles away from the passage 620. The inner surface of the second portion 530, 630 of the passage 520, 620 and the outer surface of the first end 550, 560 of second tubular member 548, 648 can also have other configurations that correspond to one another other than those illustrated in FIGS. 7 and 8.

The passage of the pusher band can include various other configurations such as different cross-sectional areas, shapes, steps and tapers that can provide, for example, better performance and/or better fit of materials. For example, the first portion can have sub-sections with different cross-sectional areas with respect to one another, and the second portion can have sub-sections with different cross-sectional areas with respect to one another. Furthermore, the passage of the pusher band can include more than two portions. For example, the passage may include a third portion between the first portion and the second portion that prevents the second tubular member from passing through the passage. As such, the third portion may have a cross-sectional area less than cross-sectional areas of the first and second portions. FIGS. 10A-E are some additional examples of pusher bands 710, 720, 730, 740, 750 that show additional configurations of passages 712, 722, 732, 742, 752, respectively. For example, the passages 712, 722, 732, 742, 752 have three, four, five, six and seven different segments, respectively, along the length of the passages 712, 722, 732, 742, 752. Each segment can have an angle that is different from angles of the neighboring segments.

Referring back to FIG. 2, the passage of the outer sheath 102 can be configured to maintain the medical device 116, such as a stent, in a compressed configuration for delivery to a deployment site within the body of the patient. For example, the medical device 116 can be positioned within a distal portion of the delivery system 100 and the second tubular member 148 can extend though the medical device 116. The medical device 116 can be positioned to be adjacent to the pusher band 118. The medical device 116 may be positioned to contact the pusher band 118 or positioned to leave a gap between the medical device 116 and the pusher band 118. The inner catheter 104 can be slideably positioned within the passage of the outer sheath 102. During deployment, the inner catheter 104 maintains the longitudinal position of the medical device 116 as the outer sheath 102 is withdrawn to expose the medical device 116 from the distal end of the delivery system 100. For example, the first handle member 113 can be held steady while the second handle member 115 can be move longitudinally toward the first handle member 113.

The second end 124 of the pusher ban 118 can be configured to provide a barrier to the medical device 116. An outer diameter of the pusher band 118 can be substantially the same as or slightly smaller than an inner diameter of the outer sheath 102 so that the medical device 116 is unable to slide between the pusher band 118 and the outer sheath 102. The second end 124 of the pusher band 118 can have any structure that provides a surface that the medical device 116 will apply a force thereon during deployment of the medical device 116. For example, as shown in FIG. 2, the second end 124 can be a substantially continuous surface extending from a position adjacent to an inner surface of the outer sheath 102 to an outer surface of the second tubular member 148.

The medical device 116 can be a stent and can be self-expanding or balloon-expandable, and can be deployed according to conventional methodology, such by an inflatable balloon catheter, by a self-deployment mechanism (after release from a catheter), or by other appropriate means. For example, the stent may be any suitable vascular stent such as the commercially available Gianturco-Roubin FLEX-STENT®, GR-II™, SUPRA-G, ZILVER®, or V FLEX coronary stents from Cook Medical (Bloomington, Ind.).

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. An inner catheter for deployment of a stent having a radially open structure, the inner catheter comprising:
    a pusher band, a first tubular member coupled to the pusher band, and a second tubular member,
    the pusher band having a passage extending from a first end to a second end of the pusher band, the passage having a first portion extending from the first end to a position between the first end and the second end, and a second portion extending from the second end to the position, the first portion of the passage having a first cross-sectional area and the second portion of the passage having a second cross-sectional area less than the first cross-sectional area to form a step at the position, an outer surface surrounding the first portion tapering to define a tapered first end, the pusher band having an outer diameter at the first end less than an outer diameter at the second end, the second end being a terminal end for applying a force to an end of the stent;
    the first tubular member comprising a first end and terminating at a second end, the first tubular member having a rigidity to resist deformation during deployment of the stent, the first tubular member entering the pusher band at the tapered first end of the pusher band, the second end of the first tubular member being within the first portion of the passage of the pusher band and abutting the step such that the second end of the first tubular member is unable to pass through the second portion; and
    the second tubular member being formed from a polymeric material and comprising a first end and a second end and defining a lumen therethrough, the lumen being sized to accommodate a wire guide, a portion of the second tubular member being within the passage of the pusher band, the second end of the second tubular member extending away from the second end of the pusher band and being configured to extend through the stent; the second tubular member is longitudinally slidable relative to the pusher band.

2. An inner catheter for deployment of a stent having a radially open structure, the inner catheter comprising:
    a pusher band, a first tubular member coupled to the pusher band, and a second tubular member,
    the pusher band having a passage extending from a first end to a second end of the pusher band, the passage having a first portion extending from the first end to a position between the first end and the second end, and a second portion extending from the second end to the position, the first portion of the passage having a first cross-sectional area and the second portion of the passage having a second cross-sectional area less than the first cross-sectional area to form a step at the position, an outer surface surrounding the first portion tapering to define a tapered first end, the pusher band having an outer diameter at the first end less than an outer diameter at the second end, the second end being a terminal end for applying a force to an end of the stent;

the first tubular member comprising a first end and terminating at a second end, the first tubular member having a rigidity to resist deformation during deployment of the stent, the first tubular member entering the pusher band at the tapered first end of the pusher band, the second end of the first tubular member being within the first portion of the passage of the pusher band and abutting the step such that the second end of the first tubular member is unable to pass through the second portion; and the second tubular member being formed from a polymeric material and comprising a first end and a second end and defining a lumen therethrough, the lumen being sized to accommodate a wire guide, a portion of the second tubular member being within the passage of the pusher band, the second tubular member being longitudinally slidable relative to the pusher band, the second end of the second tubular member extending away from the second end of the pusher band and being configured to extend through the stent.

3. An inner catheter for deployment of a stent having a radially open structure, the inner catheter comprising:

a pusher band, a first tubular member coupled to the pusher band, and a second tubular member, the pusher band having a passage extending from a first end to a second end of the pusher band, the passage having a first portion extending from the first end to a position between the first end and the second end, and a second portion extending from the second end to the position, the first portion of the passage having a first cross-sectional area and the second portion of the passage having a second cross-sectional area less than the first cross-sectional area to form a step at the position, an outer surface surrounding the first portion tapering to define a tapered first end, the pusher band having an outer diameter at the first end less than an outer diameter at the second end, the second end being configured to apply a force in an axial dimension to an end of the stent distal the pusher band during delivery, such that the second end defines the distal-most region of contact between the inner catheter and the stent during delivery;

the first tubular member comprising a first end and terminating at a second end, the first tubular member having a rigidity to resist deformation during deployment of the stent, the first tubular member entering the pusher band at the tapered first end of the pusher band, the second end of the first tubular member being within the first portion of the passage of the pusher band and abutting the step such that the second end of the first tubular member is unable to pass through the second portion; and the second tubular member being formed from a polymeric material and comprising a first end and a second end and defining a lumen therethrough, the lumen being sized to accommodate a wire guide, a portion of the second tubular member being within the passage of the pusher band, the second tubular member being longitudinally slidable relative to the pusher band, the second end of the second tubular member extending away from the second end of the pusher band and being configured to extend through the stent.

\* \* \* \* \*